United States Patent
Watanabe

(10) Patent No.: US 8,940,251 B2
(45) Date of Patent: Jan. 27, 2015

(54) SAMPLE LIQUID SUPPLY DEVICE, SAMPLE LIQUID SUPPLY DEVICE SET, AND MICROCHIP SET

(75) Inventor: Hidetoshi Watanabe, Chiba (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 13/349,874

(22) Filed: Jan. 13, 2012

(65) Prior Publication Data

US 2012/0195796 A1    Aug. 2, 2012

(30) Foreign Application Priority Data

Jan. 31, 2011 (JP) ................................. 2011-017765

(51) Int. Cl.
*B01L 3/02* (2006.01)

(52) U.S. Cl.
USPC ..... 422/512; 422/546; 73/864.74; 73/864.87; 604/162; 604/167.02; 604/239; 604/244

(58) Field of Classification Search
CPC .............. G01N 35/1079; B01L 3/0296; B01L 3/50825; B01L 3/021; A61M 5/322; A61M 25/0631; A61M 39/04; A61M 5/158; A61M 5/32; A61M 5/3202
USPC ......... 422/500–502, 504, 508–509, 511–512, 422/546, 549, 550–551, 922, 924, 931, 422/524–525; 73/863.32, 864.74, 764.87; 604/162, 167.02, 187, 188, 239, 244
See application file for complete search history.

(56) References Cited

U.S. PATENT DOCUMENTS

| | | | | |
|---|---|---|---|---|
| 4,786,471 | A * | 11/1988 | Jones et al. | 422/430 |
| 6,030,582 | A * | 2/2000 | Levy | 422/570 |
| 6,451,614 | B1 * | 9/2002 | Grob et al. | 436/161 |
| 2003/0144633 | A1 * | 7/2003 | Kirchhofer | 604/201 |
| 2007/0157709 | A1 * | 7/2007 | Gamble et al. | 73/61.55 |
| 2011/0038758 | A1 * | 2/2011 | Akaba et al. | 422/69 |
| 2012/0095409 | A1 * | 4/2012 | Lanin et al. | 604/201 |

FOREIGN PATENT DOCUMENTS

| | | |
|---|---|---|
| JP | 2004219199 | 8/2004 |
| JP | 2009284769 | 12/2009 |

* cited by examiner

*Primary Examiner* — Brian R Gordon
(74) *Attorney, Agent, or Firm* — K&L Gates LLP

(57) ABSTRACT

A sample liquid supply device includes a container tip into which the sample liquid is introduced, a hollow needle provided at one end of the container tip such that a hollow part thereof communicates with inside of the container tip, and a sealing member that covers an opening from which the sample liquid is introduced, wherein the sealing member has a puncture-sealing property achieved by elastic deformation.

10 Claims, 9 Drawing Sheets

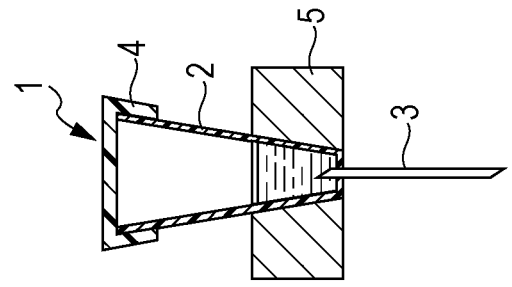
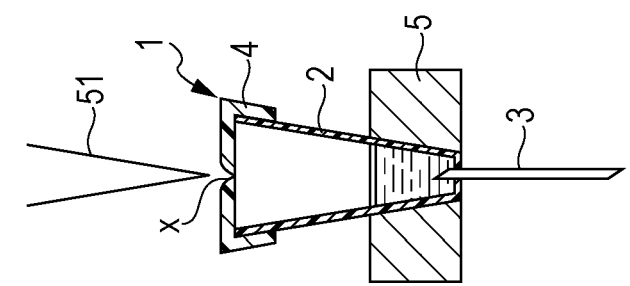
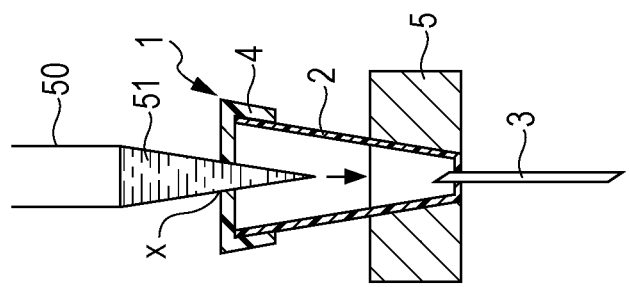
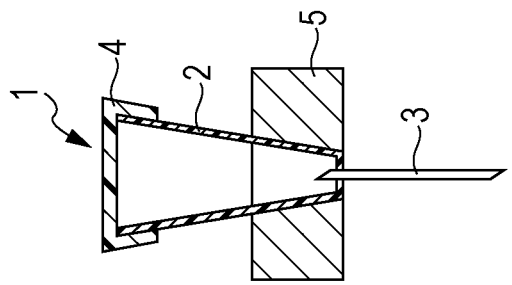

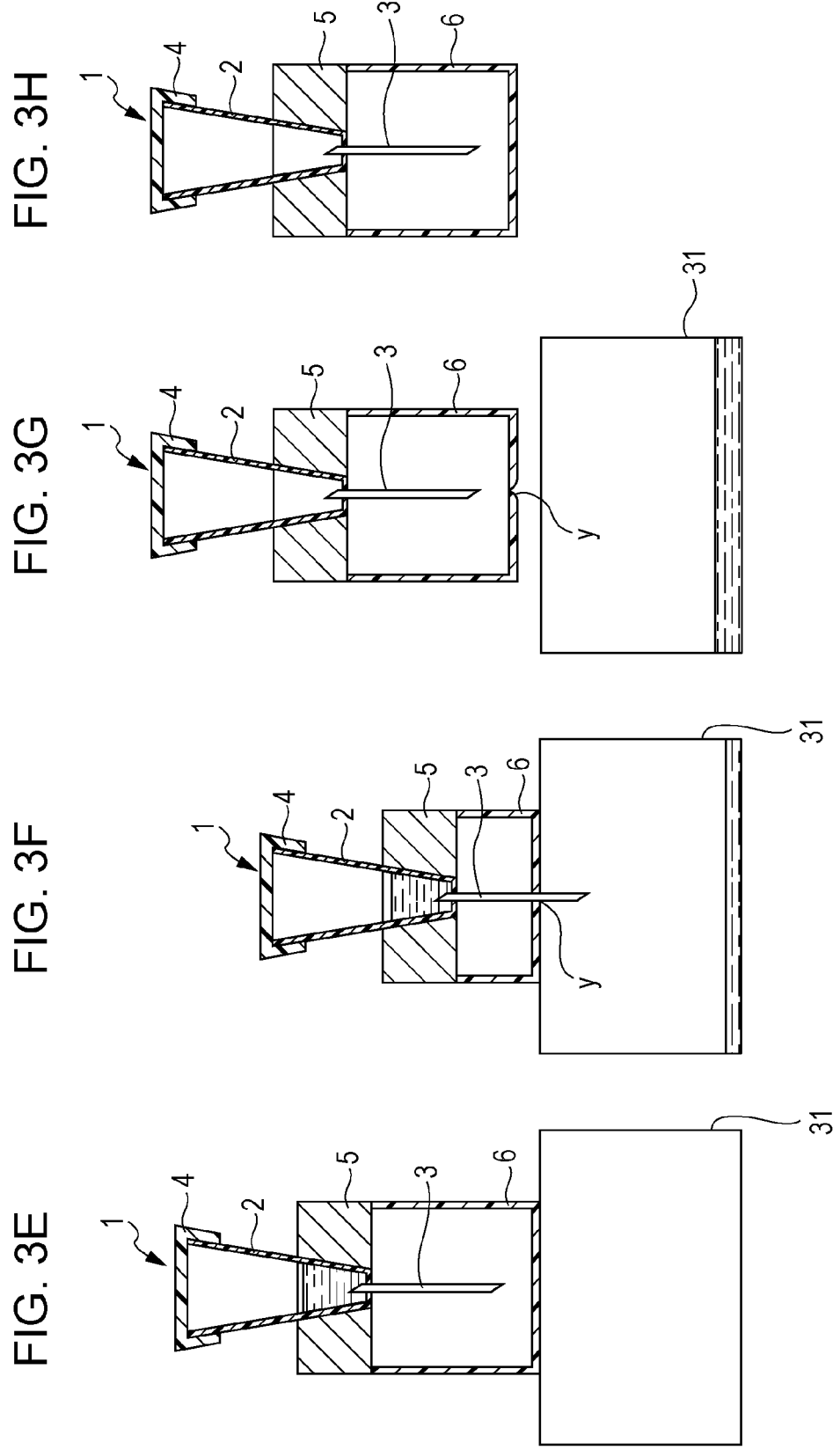

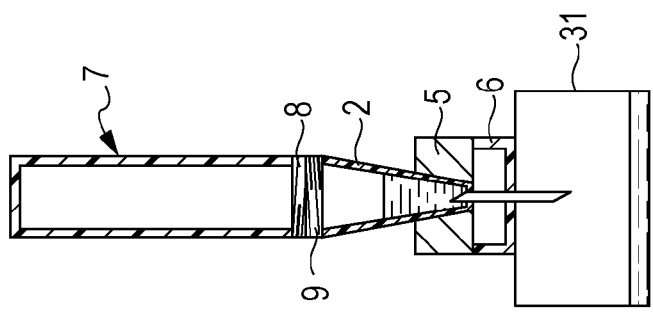
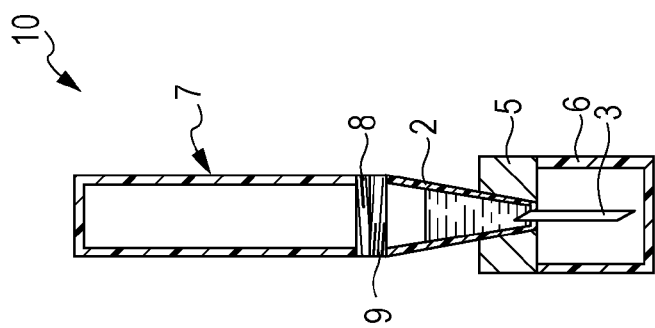
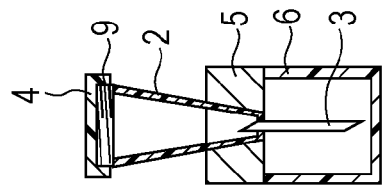
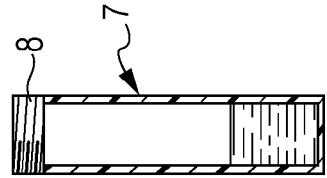
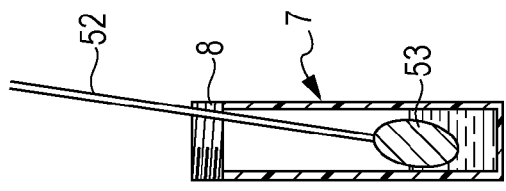

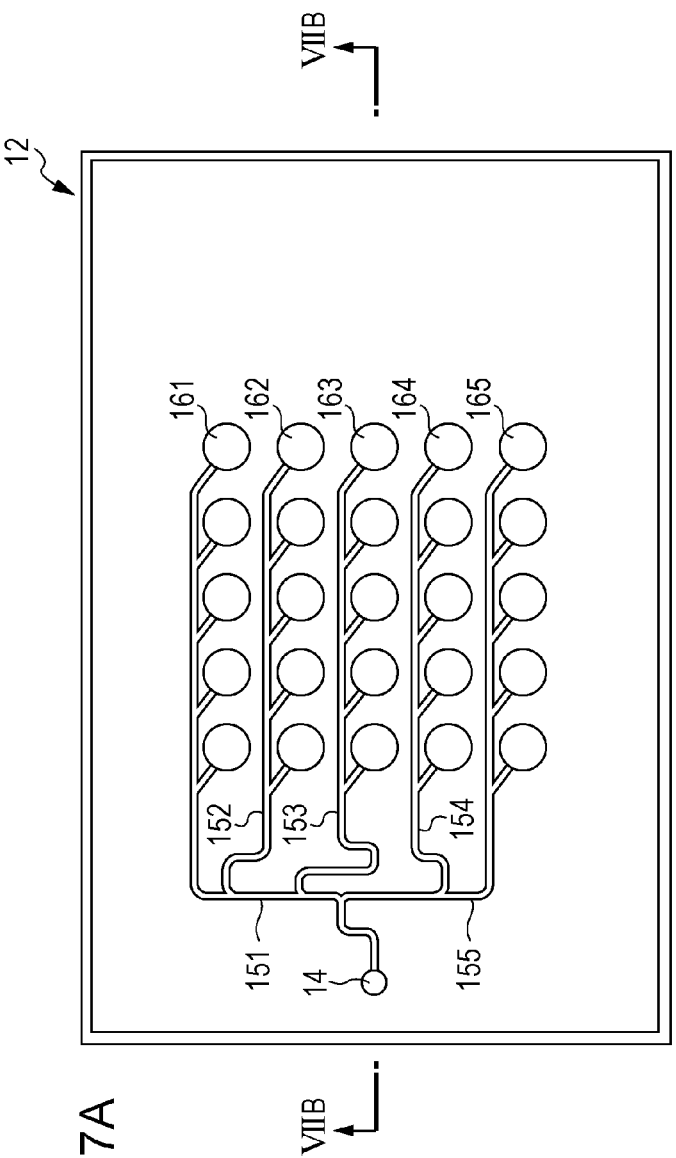
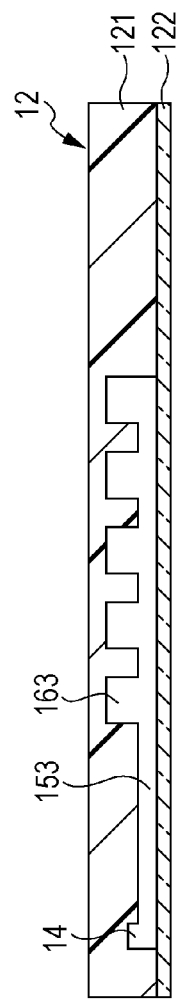
FIG. 7A
FIG. 7B

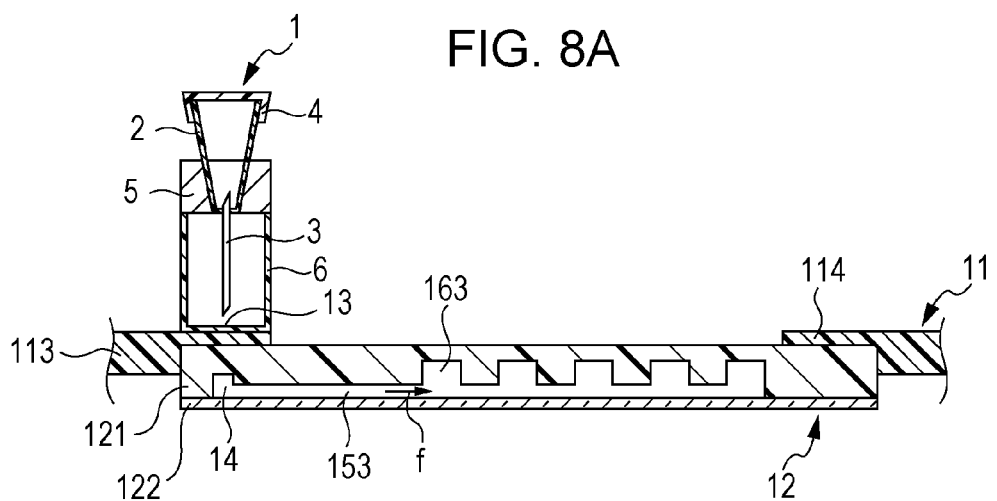
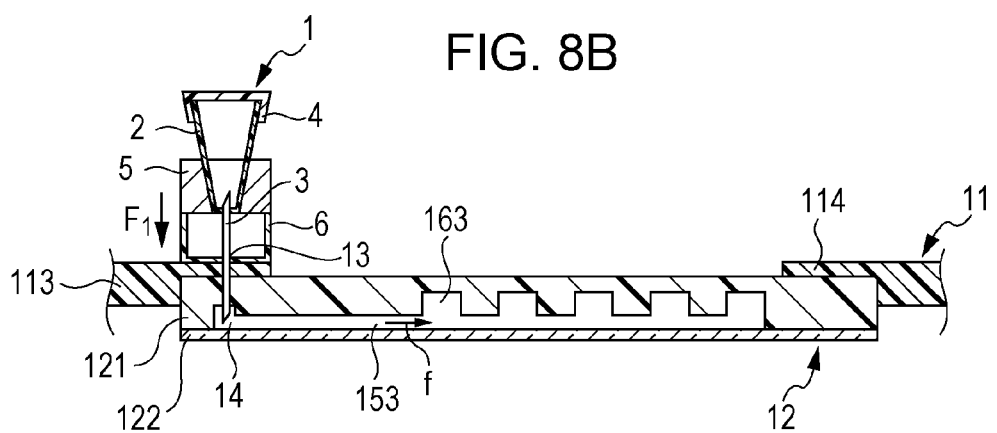
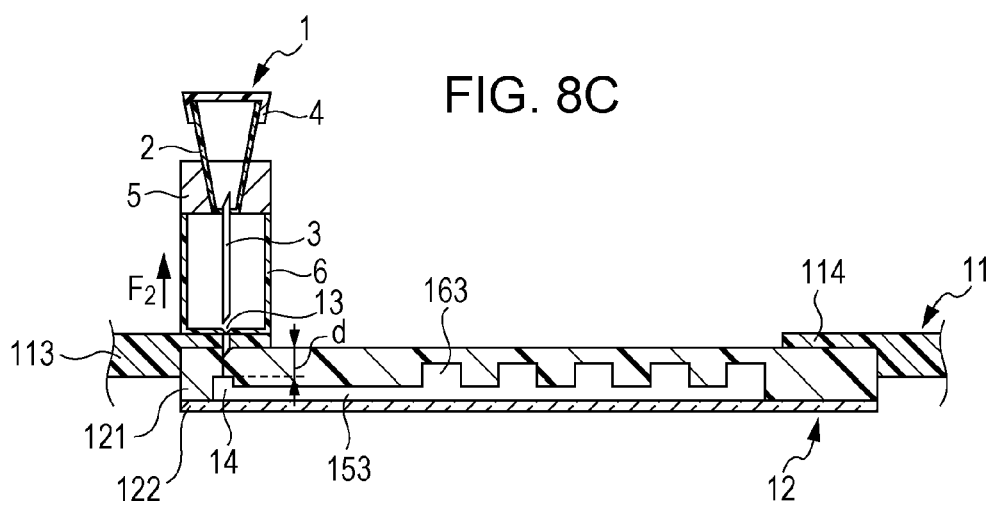

SAMPLE LIQUID SUPPLY DEVICE, SAMPLE LIQUID SUPPLY DEVICE SET, AND MICROCHIP SET

CROSS REFERENCES TO RELATED APPLICATIONS

The present application claims priority to Japanese Priority Patent Application JP 2011-017765 filed in the Japan Patent Office on Jan. 31, 2011, the entire content of which is hereby incorporated by reference.

BACKGROUND

The present disclosure relates to a sample liquid supply device, a sample liquid supply device set, and a microchip set. More particularly, the present disclosure relates to a sample liquid supply device that simply injects liquid into a hollow portion formed in a microchip.

In recent years, microchips with wells or flow paths formed on a silicon or a glass substrate have been developed by micro fabrication techniques, which are widely used in the semiconductor industry, to chemically or biologically analyze a sample liquid (for example, refer to Japanese Unexamined Patent Application Publication No. 2004-219199). These microchips have begun to be applied to electrochemical detectors in liquid chromatography, small electrochemical sensors in a medical setting, and the like.

The analysis system that employs such a microchip is called micro-total analysis system (μ-TAS), lab-on-a-chip, biochip, or the like, and has been attracting attention as a technique enabling increase in speed, efficiency, and integration in the chemical analysis and the bioanalysis, or downsizing of analyzing devices.

In the μ-TAS, only a small amount of sample is used for the analysis, and the microchip is designed for disposable use. For these reasons, the μ-TAS is expected to be suitably used for the bioanalysis that analyzes a small amount of precious sample or a large number of samples.

Examples of the μ-TAS include an optical detection device that introduces a sample in a plurality of regions provided on a microchip, and then optically inspects the sample. Such an optical detection device may include; an electrophoresis device that separates a plurality of substances contained in a solution in a flow path on a microchip by electrophoresis, and optically examines the separated substances individually; a reaction device (for example, real-time polymerase chain reaction (PCR) device) that facilitates reactions among a plurality of substances in wells on a microchip, and optically analyzes the resulting substances, and the like.

In the μ-TAS, since a very small amount of sample is used, the introduction of the sample liquid into the wells or flow paths is difficult. Sometimes, the sample liquid is prevented from entering the well or the like due to air remaining in the well or the like, and it takes a long time to be fully introduced into the wells or the like even if the sample can enter the wells or the like. In another case, bubbles may be generated in the wells or the like during the introduction of the sample liquid. As a result, the amount of the sample liquid introduced in each well or the like may vary and the variation in sample amount may lower the accuracy or efficiency of the analysis. Further, when the sample is heated in the PCR, bubbles remaining in the wells or the like may expand, and the expansion may inhibit the reaction or lower the accuracy of the analysis.

In order to facilitate the introduction of the sample liquid in the μ-TAS, for example, Japanese Unexamined Patent Application Publication No. 2009-284769 discloses a substrate that "is equipped with at least a sample-introducing part for introducing the samples, a plurality of storing parts for storing the samples, and a plurality of air-discharging parts connected to the storing parts. Two or more of the air-discharging parts are communicated with one open channel having one opened terminal." Since the substrate described above has air-discharging parts communicating to the individual containers (storing parts), the air in the container is discharged from the air-discharging parts when the sample liquid is introduced from the sample-introducing part to the containers. As a result, the containers can be easily filled with the sample liquid.

SUMMARY

As described above, in the μ-TAS and the like, the introduction of the sample liquid into the wells or flow paths may be difficult, and sometimes, the sample liquid is prevented from entering the well or the like due to air remaining therein, and it takes a long time to be fully introduced into the well or the like. Further, during the introduction of the sample liquid, bubbles may be generated in the wells or the like. In view of such problems, improvements have been made to realize the microchips that can easily introduce sample liquid in a short time and be used in highly accurate analysis.

As an example of such improvements in the μ-TAS, prevention of mixing of a foreign material such as dust in a supply container has been demanded to ensure high analysis accuracy. Further, when a sample liquid is pumped and introduced into wells or flow paths in the μ-TAS, the flow paths may have low conductivity for the solution according to the size of cross-sectional area or the shape of pattern thereof. As a result, high liquid pumping pressure has to be applied. In such a case, in order to ensure safety, prevention of spatter or leakage of the sample liquid from the supply container has been demanded.

In view of the above-mentioned problems, the present disclosure provides a sample liquid supply device that ensures high analysis accuracy and operational safety.

To solve the above-mentioned problems, according to an embodiment of the present disclosure, a sample liquid supply device includes; a container tip into which liquid is introduced; a hollow needle provided at one end of the container tip such that the hollow part of the hollow needle may communicate with inside of the container tip; and a sealing member that covers an opening from which the sample liquid is introduced, and the sealing member has a puncture-sealing property achieved by elastic deformation thereof. The sample liquid supply device may include a needle cover. The needle cover, which has a puncture-sealing property with elastic deformation, covers the hollow needle. When the hollow needle is to be used, the needle cover is punctuated by the hollow needle. In the sample liquid supply device, the sealing member may include a thin film containing a material selected from the group consisting of silicone resins, fluorine resins, and polypropylene, and the needle cover may include a thin film containing a material selected from the group consisting of silicone resins, fluorine resins, and polypropylene. In the sample liquid supply device, the container tip may include a fitting section that can fit to a container containing liquid.

Further, according to an embodiment of the present disclosure, provided is a sample liquid supply device set that includes; a container that can contain a sample liquid; a container tip that can fit to the container and into which the sample liquid contained in the container is introduced by the fitting operation; a hollow needle provided at one end of the container tip such that the hollow part of the hollow needle may communicate with inside of the container tip, and a sealing member that covers an opening from which the sample liquid is introduced, wherein the sealing member has a puncture-sealing property achieved by elastic deformation.

Further, according to an embodiment of the present disclosure, provided is a microchip set that includes; a microchip including a hollow portion therein to be filled with a sample liquid; and a sample liquid supply device including a container tip into which the sample liquid is introduced; a hollow needle provided at one end of the container tip such that a hollow part thereof may communicate with inside of the container tip, and a sealing member that covers an opening from which the sample liquid is introduced, wherein the sealing member has a puncture-sealing property achieved by elastic deformation. In the microchip set, the sample liquid supply device may include a needle cover, which has a puncture-sealing property with elastic deformation, covers the hollow needle. When the hollow needle is to be used, the needle cover is punctuated by the hollow needle.

According to the embodiments of the present disclosure, the sample liquid supply device that ensures the high analysis accuracy and the operational safety is provided.

Additional features and advantages are described herein, and will be apparent from the following Detailed Description and the figures.

BRIEF DESCRIPTION OF THE FIGURES

FIGS. 1A to 1D are cross-sectional views illustrating a sample liquid supply device according to a first embodiment of the present disclosure;

FIGS. 3E to 3H are cross-sectional views illustrating the sample liquid supply device according to the second embodiment of the present disclosure;

FIGS. 5A to 5E are cross-sectional views illustrating the sample liquid supply device according to the embodiment of the present disclosure;

FIG. 6A is a top view, FIG. 6B is a cross-sectional view along the line VIB-VIB in FIG. 6A, and FIG. 6C is a cross-sectional view along the line VIC-VIC in FIG. 6A;

FIGS. 7A and 7B illustrate a configuration of a body 12 of the microchip used in the microchip set according to the embodiment of the present disclosure; FIG. 7A is a top view, and FIG. 7B is a cross-sectional view along the line VIIB-VIIB in FIG. 7A;

FIGS. 8A to 8C illustrate steps of an operation for introducing a sample liquid into a microchip by a microchip set according to the embodiment of the present disclosure.

DETAILED DESCRIPTION

Figure 2A:
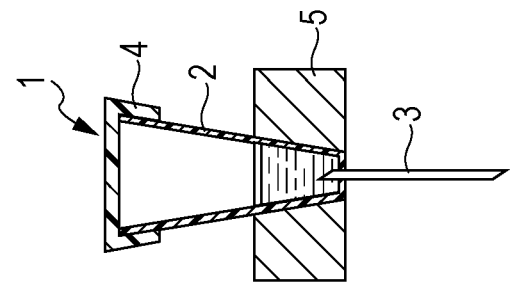
FIGS. 2A to 2D are cross-sectional views illustrating a sample liquid supply device according to a second embodiment of the present disclosure.
Figure 2B:
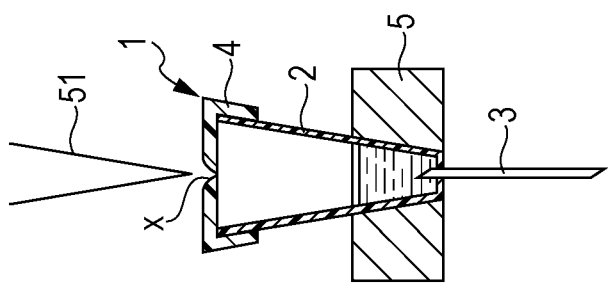
Figure 2C:
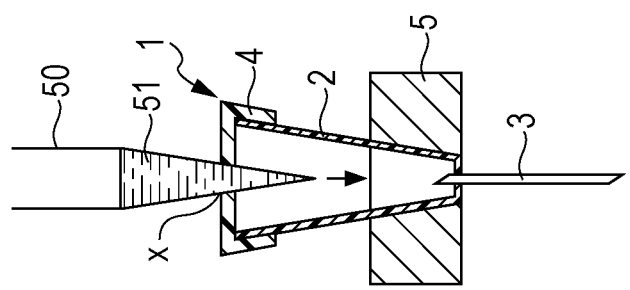
Figure 2D:
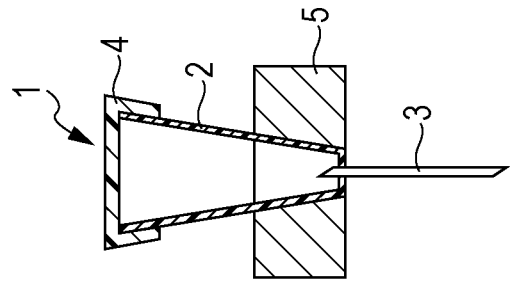

The present disclosure will be described with reference to the attached drawings according to an embodiment. The embodiments described below are only examples of typical embodiments of the present disclosure. It is noted that the scope of the present disclosure is not limited to the embodiments. The descriptions will be made in the following order.
1. Sample liquid supply device and sample liquid supply device set
(1-1) First embodiment of the sample liquid supply device
(1-2) Second embodiment of the sample liquid supply device
(1-3) Sample liquid supply device set
2. Microchip set
(2-1) First embodiment of the microchip set
(2-2) Second embodiment of the microchip set
1. Sample Liquid Supply Device and Sample Liquid Supply Device Set (1-1) First Embodiment of the Sample Liquid Supply Device FIGS. 1A to 1D are cross-sectional views illustrating a sample liquid supply device according to the first embodiment of the present disclosure.

A sample liquid supply device 1 according to the embodiment includes a container, that is, an end part of a micropipette. As illustrated in FIG. 1A, the sample liquid supply device 1 includes; a container (container tip) 2 into which a sample liquid is to be introduced, and a hollow needle 3 that is provided at one end of the container tip 2, wherein the hollow part of the hollow needle 3 communicates with the inside of the container tip 2. Further, a sealing member 4 is provided such that the member 4 covers the container tip 2 at an opening from which the sample liquid is introduced, and a supporting section 5 are formed to support the sample liquid supply device 1. The hollow needle 3 is, for example, a painless needle that is used as a needle for injection of insulin, whose outside diameter is about 0.2 mm.

The sealing member 4 seals the opening and has sufficient elasticity to allow a container 51, which is described below, to penetrate the sealing member 4. Further, as will be also described below, the sealing member 4 can seal a punctured portion by its elastic deformation after the container 51 is removed. In the present disclosure, the property to seal the punctured portion by elastic deformation of the sealing member 4 is referred to as a "puncture-sealing property" of the sealing member 4. The material of the sealing member 4 is not limited to a specific material, and various kinds of rubbers such as silicone rubber or resins such as a thermoplastic elastomer may be used. In view of the puncture-sealing property, preferably, the sealing member 4 contains a material selected from the group consisting of silicone resins, fluorine resins. A polypropylene member is preferably used as the sealing member 4 if the polypropylene member has slits to enhance the flexibility thereof. Although the shape of the sealing member 4 is not limited to a specific one, the thickness thereof is preferably thin regarding penetration by the container 51.

The sample liquid supply device 1 according to the embodiment can be obtained, for example, by inserting the hollow needle 3 into the container tip 2 from its tapered head having been provided with the supporting section 5, and by covering an opening of the container, which is to be filled with the sample liquid, with the sealing member 4. Ready-made components may serve as the container tip 2, the hollow needle 3, and the supporting section 5.

To introduce the sample liquid into the sample liquid supply device 1, first, a container 51 of a pipette 50 storing the sample liquid penetrates into the container tip 2 through the sealing member 4 at a position X marked on the sealing member (see FIG. 1B). Any position on the sealing member 4 may serve as the position X. Then, the sample liquid in the container 51 is introduced into the container tip 2 (see an arrow in FIG. 1B).

After the sample liquid is all introduced into the container tip 2, the container 51 is removed via the position X on the sealing member 4 (see FIG. 1C). In this state, on the sealing member 4, the hole is formed by puncturing with the container 51 at the position X. However, since the sealing member 4 has the above-mentioned puncture-sealing property, after the container 51 is removed, the punctured portion closes up by itself (see FIG. 1D).

As described above, the sample liquid supply device 1 may prevent the sample liquid from being contaminated by foreign materials existing outside when the sample liquid is introduced into the supply device. By using the sample liquid supply device 1 according to the embodiment, high accuracy in analysis of the sample liquid can be ensured.

Further, since the sealing member 4 covering the opening of the sample liquid supply device 1, from which the sample liquid is introduced into the container tip 2, has the puncture-sealing property, spatter or leakage of the sample liquid to the outside can be prevented during and after the infusing process. As described above, in the analysis using the sample liquid supply device 1 according to the embodiment, the safety can be ensured. Further, by preventing the spatter, generation of a difference in amount between the sample liquid to be analyzed and the sample liquid actually analyzed can be reduced. As a result, high accurate analysis of the sample liquid can be achieved.

(1-2) Second Embodiment of the Sample Liquid Supply Device

Figure 4:
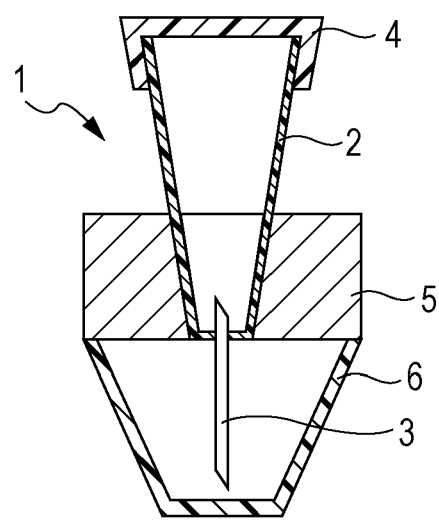
FIG. 4 is a cross-sectional view illustrating a modification of the sample liquid supply device according to the second embodiment of the present disclosure.

FIGS. 2A to 2D and FIGS. 3E to 3H are cross-sectional views illustrating a sample liquid supply device according to the second embodiment of the present disclosure. FIG. 4 is a cross-sectional view illustrating a modification of the sample liquid supply device according to the second embodiment of the present disclosure.

A sample liquid supply device 1 according to the embodiment includes a container, that is, an end part of a micropipette. As illustrated in FIG. 2A, the sample liquid supply device 1 includes; a container (container tip) 2 into which a sample liquid is to be introduced; and a hollow needle 3 that is provided at one end of the container tip 2, wherein the hollow part of the hollow needle 3 communicates with the inside of the container tip 2. Further, a sealing member 4 is provided such that the member 4 covers the container tip 2 at an opening from which the sample liquid is introduced, and a supporting section 5 are formed to support the sample liquid supply device 1. Further, the sample liquid supply device 1 includes a needle cover 6 that covers the hollow needle 3. The sample liquid supply device 1 according to the second embodiment is substantially similar to that described in the first embodiment except that the needle cover 6 is provided (see FIG. 2A). Accordingly, in the second embodiment, the functional configuration of the needle cover 6 is mainly described.

The needle cover 6 airtightly covers the needle and has sufficient elasticity to allow a hollow needle 3 to penetrate the needle cover 6 when a sample liquid is injected onto a predetermined region. Further, as will be described below, the needle cover 6 can seal a punctured portion by its elastic deformation after the hollow needle 3 is removed. In the present disclosure, the property to seal the punctured portion by elastic deformation of the needle cover 6 is also referred to as a "puncture-sealing property" of the needle cover 6 similarly to that of the sealing member 4. The material of the needle cover 6 is not limited to a specific material, and various kinds of rubbers such as silicone rubber or resins such as a thermoplastic elastomer may be used. In view of the puncture-sealing property, preferably, the needle cover 6 contains a material selected from the group consisting of silicone resins, fluorine resins. A polypropylene member is preferably used as the needle cover 6 if the polypropylene member has slits to enhance the flexibility thereof. Although the shape of the needle cover 6 is not limited to a specific one, the thickness thereof is preferably thin regarding penetration by the hollow needle 3. The method of covering the hollow needle 3 with the needle cover 6 is not limited to a specific method. For example, the needle cover 6 may be formed in a substantially columnar shape to cover the hollow needle 3 (see FIG. 2A). As illustrated in FIG. 4, the needle cover 6 may be formed such that the needle cover 6 becomes closer to the hollow needle 3 as the needle cover 6 becomes closer to the tip side of the hollow needle 3.

The sample liquid supply device 1 according to the second embodiment can be obtained by providing the needle cover 6 to the sample liquid supply device according to the first embodiment such that the needle cover 6 covers the hollow needle 3.

In the second embodiment, a method of introducing the sample liquid into the sample liquid supply device 1 is substantially similar to that according to the first embodiment. That is, the method of introducing the sample liquid illustrated in FIGS. 2A to 2D is substantially similar to the method described with reference to FIGS. 1A to 1D. Accordingly, in the description, a method of injecting the sample liquid, which is stored in the sample liquid supply device 1, into an injection region 31 via the hollow needle 3 is described with reference to FIGS. 3E to 3H.

First, in the injection of the sample liquid stored in the sample liquid supply device 1 into the injection region 31, the injection region 31 is punctured with one end of the hollow needle 3 (see FIGS. 3E and 3F). In the operation, the needle cover 6 is penetrated by the hollow needle 3 at the position of Y (see FIG. 3F). Any position on the needle cover 6 may serve as the position Y. The sample liquid stored in the sample liquid supply device 1 is injected into the injection region 31. In the injection, if the pressure in the injection region 31 is reduced, the sample liquid can be injected in a short time and easily into the injection region 31.

After the sample liquid is all injected into the injection region 31, the hollow needle 3 is removed via the position Y on the needle cover 6 (see FIG. 3G). In this state, on the needle cover 6, the hole is formed by puncturing with the hollow needle 3 at the position Y. However, since the needle cover 6 has the above-mentioned puncture-sealing property, after the hollow needle 3 is removed, the punctured portion closes up by itself (see FIG. 3H).

As described above, in the sample liquid supply device 1, in addition to the ensured high analysis accuracy concerning the sample liquid, erroneous puncture of the hollow needle 3 to a human body due to erroneous motion can be avoided since the needle cover 6 covers the hollow needle 3 before and after the injection of the sample liquid into the injection region 31. Further, if the hollow needle 3 is broken, fragments of the hollow needle 3 can be prevented from scattering around the sample liquid supply device 1. Further, it can be prevented that the sample liquid attached to the tip portion of the hollow needle 3 or the like comes in contact with a human body.

(1-3) Sample Liquid Supply Device Set

FIGS. 5A to 5E are cross-sectional views illustrating a sample liquid supply device according to a preferred embodiment of the present disclosure.

A sample liquid supply device set 10 according to the embodiment includes a container 7 in which a sample liquid is contained, and the container 7 has a fitting section 8 (see FIG. 5A). The sample liquid supply device set 10 includes a fitting section 9 that can fit to a container 7, and a sample liquid supply device 1 having the container tip 2 into which a sample liquid contained in the container 7 at the time of the fitting is to be introduced (see FIG. 5C). The sample liquid supply device further includes the hollow needle 3 that is provided at one end of the container tip 2, and the hollow part of the hollow needle 3 communicates with the inside of the container, and the sealing member 4 that covers an opening from which the liquid in the container tip 2 is introduced, and the sealing member 4 that has the puncture-sealing property by elastic deformation. That is, the sample liquid supply device according to the embodiment is substantially similar to the above-described sample liquid supply device 1 according to the second embodiment except that the fitting section 9 is provided. Accordingly, in the embodiment, with respect to the sample liquid supply device set 10, a functional configuration of the container 7 having the fitting section 8 and the fitting section 9 in the sample liquid supply device will be mainly described. As an example, similarly to the sample liquid supply device 1 according to the second embodiment of the present disclosure, the sample liquid supply device for the sample liquid supply device set 10 employs a sample liquid supply device including the needle cover 6. However, the embodiment is not limited to the example. That is, in the sample liquid supply device for the sample liquid supply device set 10, for example, similarly to the sample liquid supply device 1 according to the first embodiment of the present disclosure, the needle cover 6 may not be included.

The container 7 holds a sample 53. For example, the container 7 is a sample tube. To the container 7, as will be described below, the fitting section 8 that can fit to the fitting section 9 of the sample liquid supply device 1 is provided. In the container 7, by dissolving the sample 53 obtained by a jig 52 for sample collection such as a spatula in liquid, or purifying the liquid, processing at a preliminary step toward analysis after injection of the sample liquid into the sample liquid supply device can be performed to adjust the sample liquid. Further, although not illustrated in the drawings, to the container 7, a cap that can fit to the fitting section 8 may be provided to ensure airtightness.

The fitting section 8 and the fitting section 9 can be formed in any shape as long as the fitting section 8 and the fitting section 9 can fit to each other. For example, the fitting section 8 may be formed as a screw cap to fit to the fitting section 9 (see FIGS. 5A to 5E).

The fitting section 8 in the sample liquid supply device in the sample liquid supply device set 10 and the fitting section 9 in the container 7 according to the embodiment can be formed using a screw cap manufacturing method according to a related art.

In the sample liquid supply device set 10 according to the embodiment, to introduce a sample liquid into the sample liquid supply device 1, first, the sample liquid is prepared in the container 7 (see FIGS. 5A and 5B). That is, in the container 7, the sample 53 obtained by the jig 52 can be dissolved in a liquid. Further, the sample liquid can be purified in the container 7. The fitting section 8 of the container 7 is fit to the fitting section 9 of the sample liquid supply device 1 (see FIGS. 5C and 5D). In the operation, the sealing member 4 is opened by the container 7, and the inside of the container 7 communicates with the inside of the container tip 2. As a result, the sample liquid in the container 7 is introduced into the inside of the container tip 2 (see FIG. 5D). Then, similarly to the sample liquid supply device 1 according to the second embodiment of the present disclosure, the sample liquid is injected into the injection region 31 (see FIG. 5E).

As described above, in the sample liquid supply device set 10, similarly to the sample liquid supply device 1 according to the first and the second embodiments of the present disclosure, the airtightness in the container tip 2 can be ensured. As a result, in the sample liquid supply device set 10, while the sample liquid is prepared in the container 7, the high accuracy in the analysis of the sample liquid can be ensured. Further, similarly to the sample liquid supply device 1 according to the second embodiment of the present disclosure, the needle cover 6 is provided. Accordingly, the needle cover 6 covers the hollow needle 3 before and after the injection of the sample liquid into the injection region 31. As a result, erroneous puncture with the hollow needle 3 to a human body due to erroneous motion can be avoided. Further, if the hollow needle 3 is broken, the fragments of the hollow needle 3 can be prevented from scattering around the sample liquid supply device 1. Further, it can be prevented that the sample liquid attached to the tip portion of the hollow needle 3 or the like comes in contact with a human body.

2. Microchip Set (2-1) First Embodiment

Figure 6A:
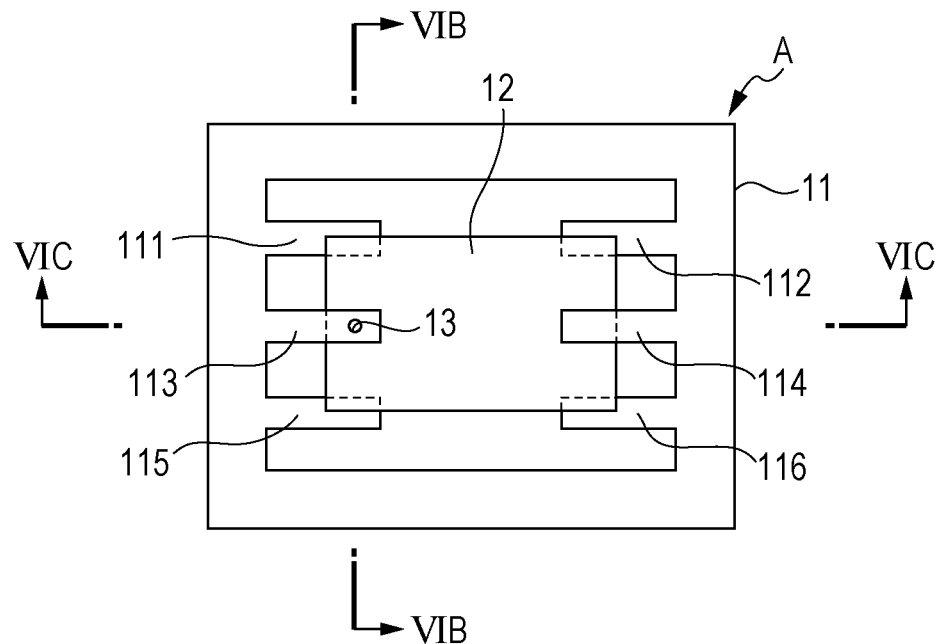
FIGS. 6A to 6C illustrate a configuration of a microchip used in a microchip set according to the embodiment of the present disclosure.
Figure 6B:
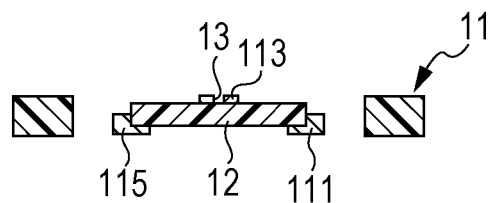
Figure 6C:
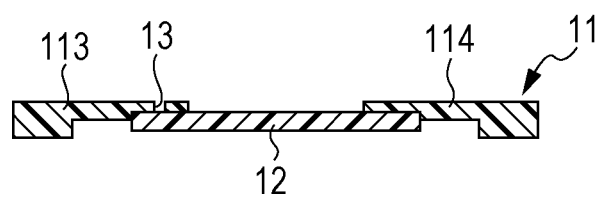

FIGS. 6A to 6C illustrate a microchip used in a microchip set according to the first embodiment of the present disclosure. FIG. 6A is a top view. FIG. 6B is a cross-sectional view along the line VIB-VIB in FIG. 6A. FIG. 6C is a cross-sectional view along the line VIC-VIC in FIG. 6A.

In the drawings, a microchip indicated by the sign A includes a body 12 in which a region where a material is introduced, and chemical analysis or bioanalysis of the material is performed, and a frame body 11 that supports the body 12. The frame body 11 supports the body 12 by arms 111, 112, 113, 114, 115, and 116 that are extended toward the center. In the arms, the arms 111, 112, 115, and 116 come in contact with the lower surface of the body 12, and support the body 12 from below. The arms 113 and 114 come in contact with the upper surface of the body 12, and support the body 12 from above. By the configuration, the body 12 is sandwiched and supported by the arms 111, 112, 115, and 116 of the lower side and the arms 113 and 114 of the upper side. The body 12 and the frame body 11 may be detachably supported by these arms. The body 12 and the frame body 11 may be bonded together on the surface the body 12 and the frame body 11 come in contact with each other, or integrally formed and connected.

In the drawings, reference numeral 13 indicates a positioning hole that functions to position a channel for injection of a solution (hereinafter, also referred to as "sample liquid") on an appropriate part (specifically, "puncture portion 14" that will be described below) on the body 12 in the injection of the sample liquid from outside into a region provided on the body 12. The positioning hole 13 is opened in the arm 113 that extends above the body 12.

FIGS. 7A and 7B illustrate the body 12 of the microchip A used in a microchip set 100 according to the first embodiment of the present disclosure. FIG. 7A is a top view. FIG. 7B is a cross-sectional view along the line VIIB-VIIB in FIG. 7A.

To the body 12, as airtight regions into which the sample liquid is injected from the outside, the following regions are formed. The puncture portion 14 serves as a region into which the sample liquid is punctured and injected from the outside. The positioning hole 13 described in FIG. 6A is opened in the arm 113, located at a position above the puncture portion 14.

Wells 161, 162, 163, 164, and 165 serve as regions for analysis of a material or a reaction product of the material contained in the sample liquid. Flow paths 151, 152, 153, 154, and 155 serve as regions for sending the sample liquid injected into the puncture portion 14 to the wells 161, 162, 163, 164, and 165 respectively.

The body 12 has five wells 161, and the wells 161 which are adjacent to each other and communicate with each other by the flow path 151. One of the wells 161 is connected to the puncture portion 14 by the flow path 151. By the configuration, the sample liquid injected into the puncture portion 14 and sent through the flow path 151 is sequentially introduced in the five wells 161. The configuration is similarly applied to the wells 162 to 165 and the flow paths 152 to 155.

In order to simultaneously start the introduction of the sample liquid injected into the puncture portion 14 into the wells 161 and the wells 162, it is preferable to form the flow path 151 and the flow path 152 such that the length of the flow path 151 to the well 161 into which the sample liquid is introduced first from the puncture portion 14 is to be the same length as the length of the flow path 152 to the well 162 into which the sample liquid is introduced first from the puncture portion 14. To form the flow path 151 and the flow path 152 to have the same total length, for example, as illustrated in FIG. 7A, it is preferable that a part that is curved or the like is provided in the flow path 152 to the well 162 into which the sample liquid is introduced first from the puncture portion 14. Preferably, the lengths of the flow paths 151, 154, and 155 to the wells 163, 164, and the 165 into which the sample liquid is introduced first from the puncture portion 14 respectively are similarly formed.

Further, as illustrated in FIG. 7A, in order to simultaneously complete the introduction of the sample liquid injected into the puncture portion 14 into the wells 161 and the wells 162, it is preferable to form the individual wells 161 and the wells 162 at equal intervals, and the total length of the flow path 151 and the total length of the flow path 152 are equal to each other. Preferably, the intervals of the wells 163 to 165 and the total lengths of the flow paths 153 to 155 are to be similarly formed.

The microchip A is formed by bonding a substrate layer $a_2$ to a substrate layer $a_1$ on which the puncture portion 14, the flow paths 151 to 155, and the wells 161 to 165 are formed. In the microchip A, by performing the bonding of the substrate layer $a_1$ and the substrate layer $a_2$ under negative pressure relative to atmospheric pressure, the regions of the flow paths 151 to 155 and the wells 161 to 165 are airtightly sealed such that the inside of the regions of the flow paths 151 to 155 and the wells 161 to 165 are to have negative pressure (for example, 1/100 atmosphere) relative to atmospheric pressure. Further, it is preferable to perform the bonding of the substrate layer $a_2$ and the substrate layer $a_2$ under vacuum such that the inside of the individual regions are airtightly sealed to be in a vacuum state.

The material forming the substrate layers $a_1$ and $a_2$ may be glass or various plastics (polypropylene, polycarbonate, cyclo-olefin polymers, and polydimethylsiloxane). Similar materials may be used for the frame body 11. Preferably, at least one of the substrate layers $a_1$ and $a_2$ is formed of a material that has elasticity. The material having the elasticity includes, in addition to silicone elastomers such as polydimethylsiloxane (PDMS), acrylic elastomers, urethane elastomers, fluorinated elastomers, styrene elastomers, epoxy elastomers, natural rubber, and the like. By forming at least one of the substrate layers $a_1$ and $a_2$ using these materials having elasticity, to the microchip A, a puncture-sealing property described below can be given.

In optical analysis of the material introduced in the wells 161 to 165, preferably, for the material forming the substrate layers $a_1$ and $a_2$, a material having a small optical error with optical transparency, low autofluorescence, and low wavelength dispersion is to be selected.

The puncture portion 14, the flow paths 151 to 155, and the wells 161 to 165 can be formed on the substrate layer $a_1$, for example, by wet etching or dry etching to a glass substrate layer, or nanoimprinting, injection forming, or cutting work to a plastic substrate layer. The individual regions may be formed to the substrate layer $a_2$, or a part of the regions may be formed to the substrate layer $a_1$, and the rest part may be formed to the substrate layer $a_2$. The substrate layer $a_1$ and the substrate layer $a_2$ can be bonded, for example, by a method according to a related art such as heat fusion bonding, an adhesive, anodic bonding, bonding using a pressure-sensitive adhesive sheet, plasma activation bonding, ultrasonic bonding, or the like.

With reference to FIGS. 8A to 8C, a method of introducing the sample liquid into the microchip A in the microchip according to the first embodiment of the present disclosure is described. FIGS. 8A to 8C illustrate cross-sectional views of the microchip A, along the line VIC-VIC in FIG. 6A.

In the microchip set illustrated in FIGS. 8A to 8C, as the sample liquid supply device 1, the sample liquid supply device according to the second embodiment of the present disclosure is described, however, the sample liquid supply device 1 is not limited to the example. That is, as the sample liquid supply device 1, the sample liquid supply device according to the first embodiment of the present disclosure can be used. In place of the sample liquid supply device 1, the sample liquid supply device set 10 according to the embodiment of the present disclosure described with reference to FIGS. 5A to 5E may be used.

In the introduction of the sample liquid into the microchip A, as illustrated in FIGS. 8A and 8B, the hollow needle 3 in the sample liquid supply device 1 penetrates the needle cover 6 and the substrate layer $a_1$, and the sample liquid is injected into the puncture portion 14. As described with reference to FIGS. 2 and 3, the sample liquid injected into the puncture portion 14 is the sample liquid that is injected into the container tip 2 by the penetration of the container 51 into the sealing member 4. In the drawings, the arrow $F_1$ indicates the puncture direction of the channel 4. The channel 4 is punctured from the surface of the substrate layer $a_1$ such that the tip portion reaches the space in the puncture portion 14 through the substrate layer $a_1$.

In the puncture, the hollow needle 3 is inserted through the positioning hole 13 opened on the arm 113 of the frame body 11, the hole 13 is located above the puncture portion 14, and penetrates the substrate layer $a_1$. As described above, by puncturing the substrate layer $a_1$ with the hollow needle 3 by inserting the hollow needle 3 using the target of the positioning hole 13 preliminarily provided above the puncture portion 14, the hollow needle 3 is positioned to the puncture portion 14, and the tip portion of the hollow needle 3 can surely reach the space in the puncture portion 14.

The sample liquid injected from the outside into the puncture portion 14 is sent through the flow paths 151 to 155 (see the arrow f in the drawings), and introduced into the wells 161 to 165. In the microchip A, the inside of the puncture portion 14, the flow paths 151 to 155, and the wells 161 to 165 are adjusted to have negative pressure relative to atmospheric pressure. Accordingly, in a state the tip portion of the hollow needle 3 reaches the space in the puncture portion 14, if the state is maintained for a certain period of time, the sample liquid is sucked by the negative pressure and easily introduced into each region. Further, if the inside of each region is in a vacuum state, the air does not exist in the each region. In such a state, the introduction of the sample liquid is not difficult and bubbles are not generated.

After the introduction of the sample liquid, as illustrated in FIG. 8C, the hollow needle 3 is withdrawn, and the punctured portion on the substrate layer $a_1$ is sealed. In the drawing, the arrow $F_2$ indicates the withdrawal direction of the channel 4. By forming the substrate layer $a_1$ using a material having elasticity such as PDMS, after the channel 4 is withdrawn, the punctured portion can close up by itself by the restoring force generated by the elastic deformation. In the embodiment of the present disclosure, the sealing of the punctured portion by itself by the elastic deformation of the substrate layer is referred to as a "puncture-sealing property" of the substrate layer.

After the introduction of the sample liquid, the needle cover 6 is punctured with the hollow needle 3 and the hole is formed. However, since the needle cover 6 has the puncture-sealing property, after the hollow needle 3 is removed, the punctured portion closes up by itself.

In order to ensure the puncture-sealing property of the substrate layer $a_1$, the thickness (in the drawing, see reference sign d) of the substrate layer from the surface of the substrate layer to the space in the puncture portion 14 at the punctured portion is to be set in an appropriate range depending on the material of the substrate layer $a_1$ and the diameter of the channel 4. In a case where the microchip A is to be heated in the analysis, the thickness d is to be set such that the puncture-sealing property is not lost by the increase in the inner pressure due to the heating.

In order to ensure the puncture-sealing property by the elastic deformation of the substrate layer $a_1$, preferably, as the hollow needle 3, a needle having the smallest diameter possible is used. Specifically, a painless needle that is used for injection of insulin, the needle having the tip outside diameter of about 0.2 mm is preferably used. In order to facilitate the injection of the sample liquid, to a base of the painless needle, a tip portion obtained by cutting a tip portion of a general-purpose micropipette may be connected. By the tip portion, in puncturing the puncture portion 14 with the painless needle in a state the sample liquid is filled in the tip portion, due to the negative pressure in the microchip A, the sample liquid in the tip portion connected to the painless needle can be sucked and injected into the puncture portion 14.

In a case where a painless needle having the tip outside diameter of 0.2 mm is used as the hollow needle 3, preferably, the thickness d of the substrate layer $a_1$ including PDMS is 0.5 mm or greater, and if heating is performed, 0.7 mm or greater.

As described above, in the microchip set according to the embodiment employs the sample liquid supply device 1 that has the sealing member 4. Accordingly, in the injection of the sample liquid into the inside and after the injection, spatter or leakage of the sample liquid to the outside, and the like can be prevented. As a result, in the analysis using the microchip set according to the embodiment, the safety can be ensured. Further, by preventing the spatter, generation of a difference between the amount of the quantified sample liquid and the amount of the sample liquid in the analysis can be reduced. As a result, in the analysis concerning the sample liquid, the high accuracy can be ensured. Further, since the sample liquid supply device 1 also has the needle cover 6, before and after the introduction of the sample liquid, the needle cover 6 covers the hollow needle 3. As a result, erroneous puncture with the hollow needle 3 to a human body due to erroneous motion can be avoided. Further, if the hollow needle 3 is broken, the fragments of the hollow needle 3 can be prevented from scattering around the sample liquid supply device 1. Further, it can be prevented that the sample liquid attached to the tip portion of the hollow needle 3 or the like comes in contact with a human body.

Further, in the microchip A according to the embodiment, in the introduction of the sample liquid, by inserting the hollow needle 3 through the positioning hole 13 provided to the arm 113 of the frame body 11 and puncturing the body 12, the hollow needle 3 can accurately puncture the puncture portion 14 of the body 12. Accordingly, in the microchip according to the embodiment, in a very small region, the sample liquid can be accurately and easily introduced. Further, it can be prevented that outside air leaks in the region, and the suction of the sample liquid by the negative pressure becomes difficult or failure due to puncture to an inappropriate portion in the body 12 with the hollow needle 3. Further, erroneous puncture to a human body or the like with the hollow needle 3 can be prevented, and the operational safety can be increased.

In the embodiment, to the microchip A, the five sets of the five wells communicating with each other by the one flow path, the total of 25 wells are provided. In the microchip according to the embodiment of the present disclosure, the number of the wells to be provided can be any number, and the positions of the wells are any positions. Further, the shape of the wells is not limited to the cylindrical shape illustrated in the drawings. Further, the configuration of the flow paths for sending the sample liquid injected into the puncture portion 14 to each well is not limited to the example illustrated in the drawings. In the embodiment, the substrate layer $a_1$ includes an elastic material, and the puncture with the hollow needle 3 is performed from the surface of the substrate layer $a_1$. However, the puncture with the hollow needle 3 may be performed from the surface of the substrate layer $a_2$. In such a case, the substrate layer $a_2$ may include an elastic material to give the puncture-sealing property.

(2-2) Second Embodiment

Figure 9A:
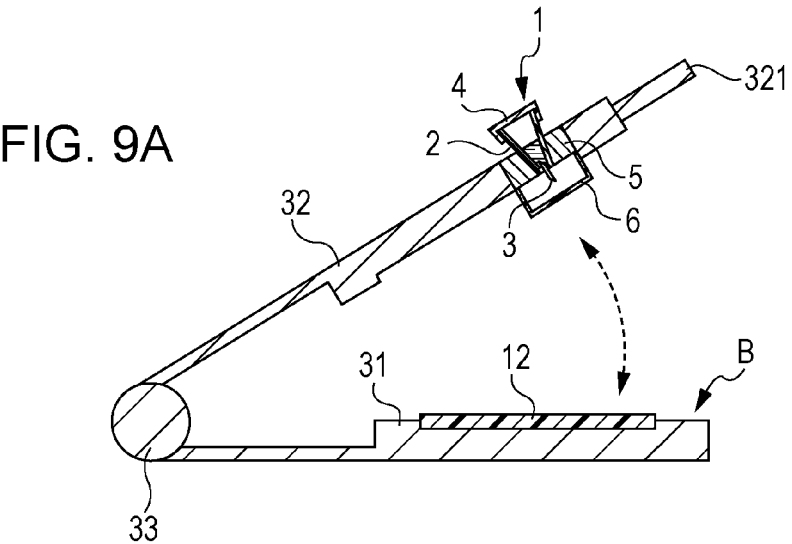
FIGS. 9A to 9C illustrate another configuration of the microchip used in the microchip set and steps of an operation for introducing a sample liquid into a microchip by a microchip set according to the embodiment of the present disclosure.
Figure 9B:
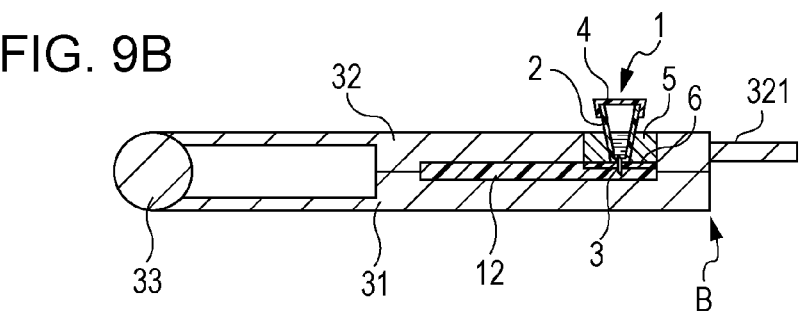
Figure 9C:
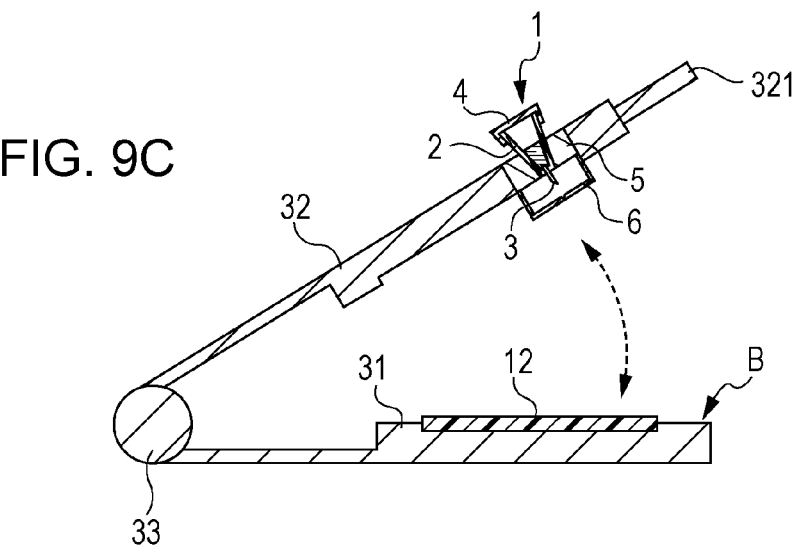

FIGS. 9A to 9C illustrate a configuration of a microchip set and a method of introducing a sample liquid according to the second embodiment of the present disclosure.

In the drawings, a microchip indicated by the sign B includes the body 12 on which a region where a material is introduced, and chemical analysis or bioanalysis of the material is performed is provided. The body 12 of the microchip B is similar to the above-described body 12 of the microchip A, and accordingly, the description is omitted in the description below. The microchip B, in addition to the body 12, includes a first member 31 and a second member 32.

In the drawings, as the sample liquid supply device 1, the sample liquid supply device according to the second embodiment of the present disclosure is described, however, the sample liquid supply device 1 is not limited to the example. That is, as the sample liquid supply device 1, the sample liquid supply device according to the first embodiment of the present disclosure can be used. In place of the sample liquid supply device 1, the sample liquid supply device set 10 according to the embodiment of the present disclosure described with reference to FIGS. 5A to 5E may be used.

On the first member 31, the body 12 is disposed and held. In order to accurately dispose the microchip B on a predetermined position on the upper surface of the first member 31, a positioning pin may be provided on the side of the first member 31, and a fitting hole for the pin may be provided on the side of the body 12. Alternatively, using the outer shape of the body 12, a method of fitting the body 12 onto a predetermined position on the upper surface of the first member 31 may be employed.

In the second member 32, the sample liquid supply device 1 for externally injecting the sample liquid into a region provided in the body 12 is supported such that the sample liquid supply device 1 faces the body 12 that is being supported by the first member 31. One end of the first member 31 and one end of the second member 32 are connected with a hinge 33, and opening and closing operation of the first member 31 and the second member 32 with a fulcrum of the hinge 33 can be performed (see the arrow of the dotted line in FIG. 9A). The supporting position of the body 12 by the first member 31 and the supporting position of the channel 4 by the second member 32 are designed such that in a state the hinge 33 is closed (see FIG. 9B), the hollow needle 3 is positioned to the puncture portion 14 of the body 12 (see FIGS. 8).

The material forming the first member 31 and the second member 32 may be glass, various metals, or various plastics. The body 12, the first member 31, and the second member 32 may be different members, or may be an integrally formed member.

As the member for openably or closably connecting the first member 31 and the second member 32, in place of the hinge 33, a rotary damper may be used. The use of the rotary damper enables stable opening and closing operation of the first member 31 and the second member 32. Between the first member 31 and the second member 32 whose one ends are connected by the hinge 33, a spring member that has elasticity in the open-close direction may be connected, or a stopper mechanism for regulating the opening and closing operation within a predetermined range may be provided. The use of these members enables stable opening and closing operation of the first member 31 and the second member 32, and increase in the operability. In the drawings, reference numeral 321 denotes a handle held in the opening and closing operation of the second member 32 to the first member 31.

In the microchip according to the embodiment, in the introduction of the sample liquid, by closing the hinge 33 in the state that the body 12 is supported by the first member 31 and the channel 4 is supported by the second member 32 respectively, the puncture of the channel 4 to the puncture portion 14 of the body 12 can be accurately performed. Accordingly, in the microchip according to the embodiment, in the very small region, the sample liquid can be accurately and easily introduced. Further, it can be prevented that outside air leaks in the region, and the suction of the sample liquid by the negative pressure becomes difficult or failure due to puncture to an inappropriate portion in the body 12 with the channel 4. Further, erroneous puncture to a human body or the like with the channel 4 can be prevented, and the operational safety can be increased.

The microchip set according to the embodiment employs the sample liquid supply device 1 that has the sealing member 4. Accordingly, in the injection of the sample liquid into the inside and after the injection, spatter or leakage of the sample liquid to the outside, and the like can be prevented. As a result, in the analysis using the microchip set according to the embodiment, the safety can be ensured. Further, by preventing the spatter, generation of a difference between the amount of the quantified sample liquid and the amount of the sample liquid in the analysis can be reduced. As a result, in the analysis concerning the sample liquid, the high accuracy can be ensured. Further, since the sample liquid supply device 1 also has the needle cover 6, before and after the introduction of the sample liquid, the needle cover 6 covers the hollow needle 3. As a result, erroneous puncture with the hollow needle 3 to a human body due to erroneous motion can be avoided. Further, if the hollow needle 3 is broken, the fragments of the hollow needle 3 can be prevented from scattering around the sample liquid supply device 1. Further, it can be prevented that the sample liquid attached to the tip portion of the hollow needle 3 or the like comes in contact with a human body.

The sample liquid used in the above-described embodiments is not limited to a specific sample liquid. For example, various kinds of samples containing nucleic acids such as a nasal swab sample from a patient who is suspected of being infected with influenza may be used.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A sample liquid supply device comprising:
    a container tip including an opening, the container tip configured for a sample liquid to be introduced;
    a hollow needle provided at one end of the container tip such that a hollow part thereof communicates with inside of the container tip;
    a needle cover that covers the hollow needle, the needle cover configured to be punctured by the hollow needle and having a puncture-sealing property achieved by elastic deformation, wherein before the needle cover is punctured by the hollow needle, the needle cover covers all of the hollow needle exposed from the container tip and wherein the needle cover is elastically deformed when punctured by the hollow needle;
    wherein the elastic deformation comprises the needle cover having a first length before the needle cover is punctured by the hollow needle and a smaller length than the first length when the needle cover is punctured by the hollow needle; and
    a sealing member that covers the opening from which the sample liquid is introduced, wherein the sealing member has a puncture-sealing property achieved by elastic deformation, and the sealing member is configured to seal the sample liquid within the container tip between the one end provided with the hollow needle and the sealing member.

2. The sample liquid supply device according to claim 1, wherein the hollow needle communicates with the inside of the container tip without puncturing the sealing member.

3. The sample liquid supply device according to claim 1, wherein the sealing member includes a film containing a material selected from the group consisting of silicone resins, fluorine resins, and polypropylene.

4. The sample liquid supply device according to claim 1, wherein the needle cover includes a film containing a material selected from the group consisting of silicone resins, fluorine resins, and polypropylene.

5. The sample liquid supply device according to claim 1, wherein the container tip includes a fitting section being fittable to a container containing liquid.

6. The sample liquid supply device according to claim 1, wherein the sealing member includes slits.

7. The sample liquid supply device according to claim 1, wherein the needle cover contains a material selected from the group consisting of silicone resins, fluorine resins, silicone rubber, polypropylene, and thermoplastic elastomers.

8. The sample liquid supply device according to claim 1, wherein the needle cover is punctured by the hollow needle at an end located distal to the container tip.

9. A sample liquid supply device set comprising:
- a container configured to contain a sample liquid;
- a container tip, including an opening, that is fittable to the container and into which the sample liquid contained in the container is introduced by a fitting operation;
- a hollow needle provided at one end of the container tip such that a hollow part thereof communicates with inside of the container tip;
- a needle cover that covers the hollow needle, the needle cover configured to be punctured by the hollow needle and having a puncture-sealing property achieved by elastic deformation, wherein before the needle cover is punctured by the hollow needle, the needle cover covers all of the hollow needle exposed from the container tip and wherein the needle cover is elastically deformed when punctured by the hollow needle;
- wherein the elastic deformation comprises the needle cover having a first length before the needle cover is punctured by the hollow needle and a smaller length than the first length when the needle cover is punctured by the hollow needle; and
- a sealing member that covers the opening from which the sample liquid is introduced, wherein the sealing member has a puncture-sealing property achieved by elastic deformation, and the sealing member is configured to seal the sample liquid within the container tip between the one end provided with the hollow needle and the sealing member.

10. A microchip set comprising:
- a microchip including a hollow portion therein to be filled with a sample liquid; and
- a sample liquid supply device including a container tip having an opening, the container tip configured for the sample liquid to be introduced, a hollow needle provided at one end of the container tip such that a hollow part thereof communicates with inside of the container tip, a needle cover that covers the hollow needle, the needle cover configured to be punctured by the hollow needle and having a puncture-sealing property achieved by elastic deformation, wherein before the needle cover is punctured by the hollow needle, the needle cover covers all of the hollow needle exposed from the container tip and wherein the needle cover is elastically deformed when punctured by the hollow needle, wherein the elastic deformation comprises the needle cover having a first length before the needle cover is punctured by the hollow needle and a smaller length than the first length when the needle cover is punctured by the hollow needle; and a sealing member that covers the opening from which the sample liquid is introduced, wherein the sealing member has a puncture-sealing property achieved by elastic deformation, and the sealing member is configured to seal the sample liquid within the container tip between the one end provided with the hollow needle and the sealing member.

* * * * *